(12) United States Patent
Nagai et al.

(10) Patent No.: US 11,648,088 B2
(45) Date of Patent: May 16, 2023

(54) COUPLING MEMBER, AND MOUTHPIECE EQUIPPED WITH COUPLING MEMBER

(71) Applicant: Mitsui Chemicals, Inc., Tokyo (JP)

(72) Inventors: Hideyuki Nagai, Iwakuni (JP); Takashi Yukita, Chiba (JP); Maki Yamamoto, Sodegaura (JP); Yasufumi Tsuchiya, Funabashi (JP); Walid Raad, New York, NY (US)

(73) Assignee: RESPIRE MEDICAL HOLDINGS LLC, Brookyln, NY (US)

( * ) Notice: Subject to any disclaimer, the term of this patent is extended or adjusted under 35 U.S.C. 154(b) by 416 days.

(21) Appl. No.: 16/083,923

(22) PCT Filed: Jun. 21, 2017

(86) PCT No.: PCT/JP2017/022917
§ 371 (c)(1),
(2) Date: Sep. 11, 2018

(87) PCT Pub. No.: WO2018/016258
PCT Pub. Date: Jan. 25, 2018

(65) Prior Publication Data
US 2019/0110866 A1 Apr. 18, 2019

(30) Foreign Application Priority Data

Jul. 19, 2016 (JP) .............................. JP2016-141424
Jul. 19, 2016 (JP) .............................. JP2016-141425

(51) Int. Cl.
*A61C 7/08* (2006.01)
*A61C 7/36* (2006.01)
*A61F 5/56* (2006.01)

(52) U.S. Cl.
CPC ................. *A61C 7/08* (2013.01); *A61C 7/36* (2013.01); *A61F 5/566* (2013.01)

(58) Field of Classification Search
CPC ..... A61C 7/36; A61C 7/08; A61C 7/10; F16B 23/0038; F16B 7/06; A61F 5/56; A61F 5/58; A61F 2005/563; A61F 5/566
(Continued)

(56) References Cited

U.S. PATENT DOCUMENTS 5,183,388 A * 2/1993 Kumar .................... A61C 7/36
433/19
5,879,157 A 3/1999 Scheu
(Continued)

FOREIGN PATENT DOCUMENTS

DE       202012005525 U1   9/2012
DE    20 2015 000 051 U1   2/2015
EP          2 143 397 A1   1/2010

OTHER PUBLICATIONS

"Rod" definition by Mariam-Webster, https://www.merriam-webster.com/dictionary/rod (Year: 2022).*
(Continued)

*Primary Examiner* — Rachael E Bredefeld
*Assistant Examiner* — Trisha Talapatra
(74) *Attorney, Agent, or Firm* — Buchanan, Ingersoll & Rooney PC

(57) ABSTRACT

A coupling member includes a sliding member and a sleeve. The sliding member has one axial direction end portion coupled to a first attachment portion provided at a first attachment that is mounted to one of a maxilla or a mandible. The sleeve has one axial direction end portion coupled to a second attachment portion provided at a second attachment that is mounted to the other of the maxilla and the mandible. The sliding member is inserted into the sleeve so as to be slidable. A restricting section is formed at the sleeve between two axial direction end portions of the sleeve so as to restrict (Continued)

sliding of the sliding member in both directions along an axial direction of the sliding member.

12 Claims, 14 Drawing Sheets

(58) Field of Classification Search
USPC .................................. 128/848; 433/6–7, 19
See application file for complete search history.

(56) References Cited

U.S. PATENT DOCUMENTS

| | | | | |
|---|---|---|---|---|
| 6,877,982 | B2* | 4/2005 | Williams | A61C 7/36 433/7 |
| 9,198,741 | B2* | 12/2015 | Morin | A61C 7/36 |
| 2002/0025502 | A1* | 2/2002 | Williams | A61C 7/10 433/7 |
| 2003/0064344 | A1* | 4/2003 | Vazquez | A61C 7/36 433/19 |
| 2007/0190477 | A1* | 8/2007 | Sheikh | A61C 7/36 433/19 |
| 2007/0224567 | A1 | 9/2007 | Robson | |
| 2011/0000495 | A1 | 1/2011 | Ash | |
| 2012/0070797 | A1* | 3/2012 | Edgren | A61C 7/36 433/22 |
| 2013/0177861 | A1* | 7/2013 | Hayes | A61C 7/20 433/24 |
| 2014/0224257 | A1 | 8/2014 | Abramson | |
| 2014/0255866 | A1* | 9/2014 | Faust | A61C 7/20 433/24 |
| 2014/0326253 | A1 | 11/2014 | Baratier et al. | |
| 2018/0263806 | A1* | 9/2018 | Toussaint | A61F 5/566 |
| 2020/0345463 | A1* | 11/2020 | Dischinger | A61C 7/36 |

OTHER PUBLICATIONS

International Search Report (PCT/ISA/210) dated Sep. 12, 2017, by the Japanese Patent Office as the International Searching Authority for International Application No. PCT/JP2017/022917.

Written Opinion (PCT/ISA/237) dated Sep. 12, 2017, by the Japanese Patent Office as the International Searching Authority for International Application No. PCT/JP2017/022917.

Partial Supplementary European Search Report dated Feb. 12, 2020, by the European Patent Office in corresponding European Patent Application No. 17830778.1. (12 pages).

Notice of Reasons for Rejection dated Dec. 17, 2019, by the Japanese Patent Office in corresponding Japanese Patent Application No. 2018-528456 and an English translation of the Office Action (8 pages).

* cited by examiner

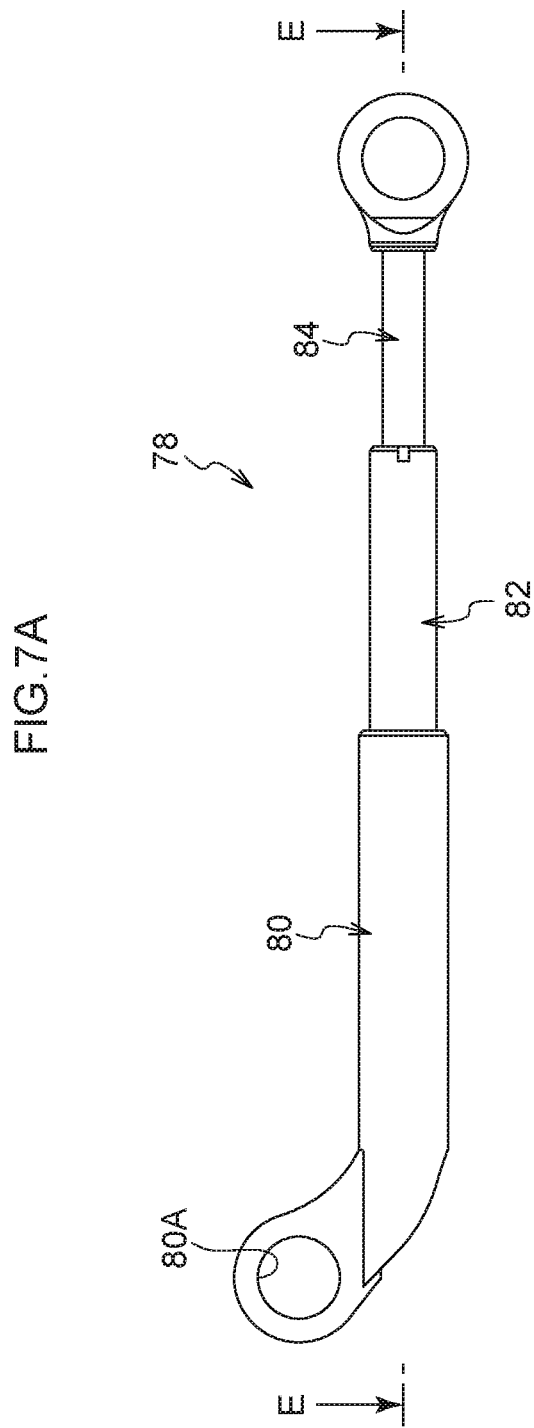

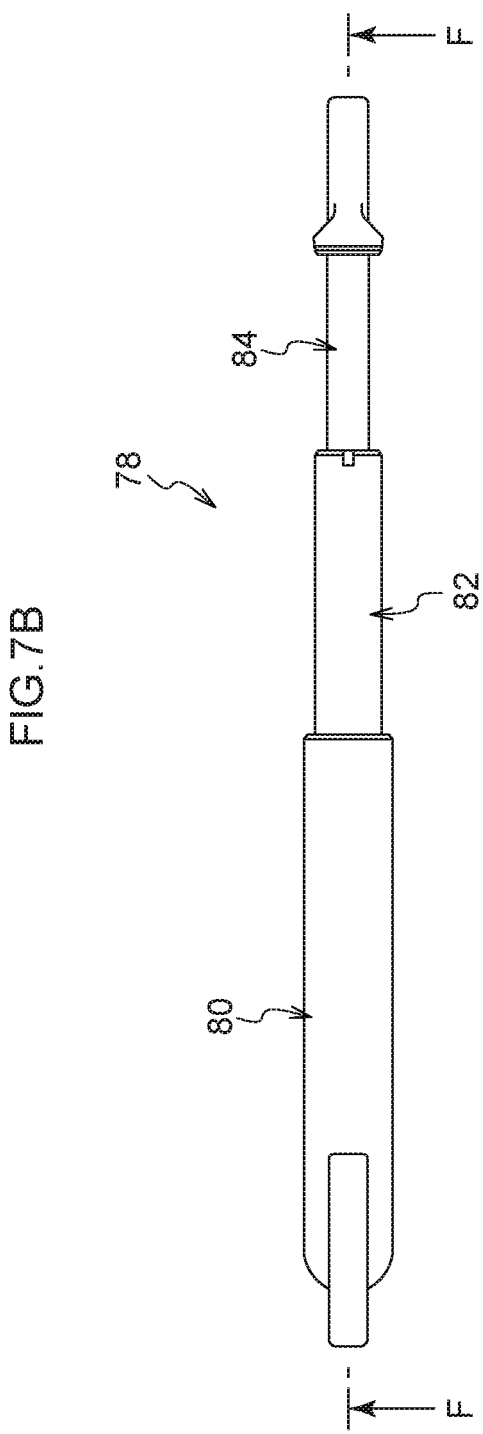

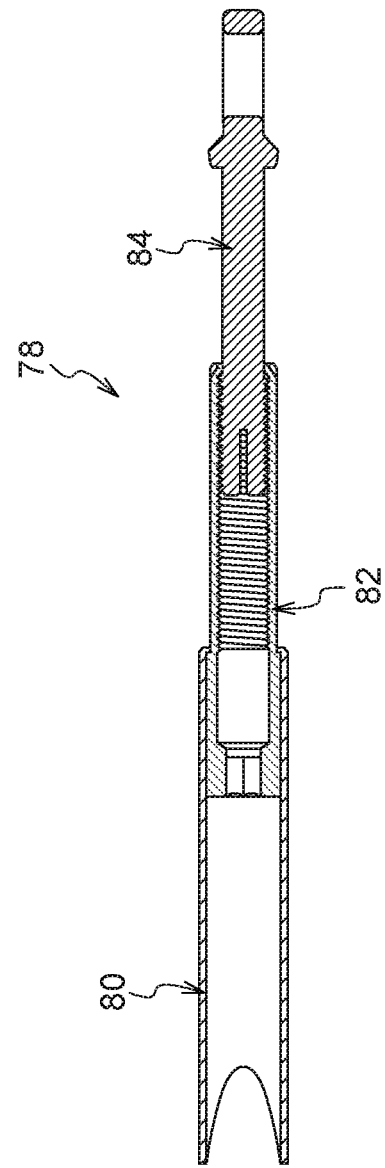

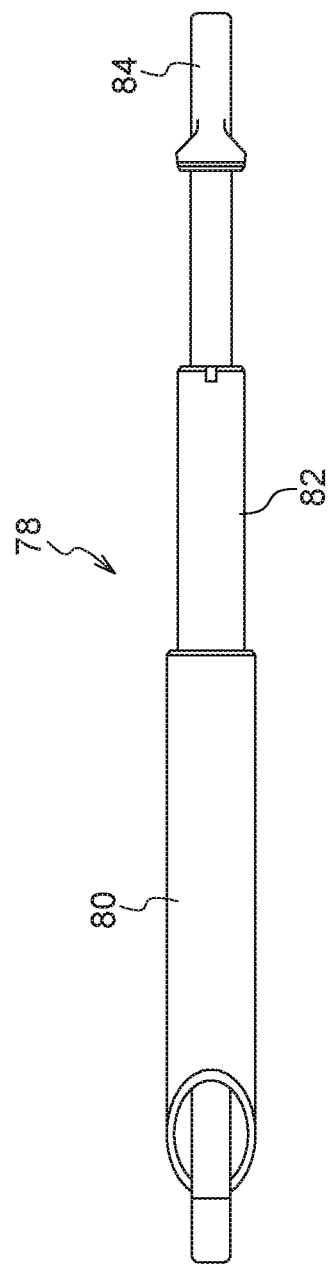

COUPLING MEMBER, AND MOUTHPIECE EQUIPPED WITH COUPLING MEMBER

TECHNICAL FIELD

The present disclosure relates to a coupling member, and to a mouthpiece equipped with a coupling member.

BACKGROUND ART

Hitherto, medical mouthpieces have been employed in the treatment of sleep apnea syndrome, temporomandibular joint disorders, and the like. An example of such a mouthpiece is a dental brace disclosed in Patent Document 1. This dental brace includes a connection member to connect a maxillary brace and a mandibular brace together, an extendible sleeve and an extendible rod that are attached to the connection member to adjust a relative position between the maxillary brace and the mandibular brace, and a nut to adjust the length of the extendible rod.

Moreover, a dental brace including a maxillary brace that fits to maxillary dentition, a mandibular brace that fits to mandibular dentition, and a bite system that connects the maxillary brace and the mandibular brace together, is disclosed, for example in Patent Document 2.

LIST OF PATENT DOCUMENT

Patent Document 1: Specification of German Patent Application Publication No. 202012005525
Patent Document 2: Specification of US Patent Application Publication No. 2007/0224567

SUMMARY OF INVENTION

Technical Problem

In the dental brace disclosed in Patent Document 1, the nut to adjust the length of the extendible rod is employed as a stopper that abuts the connection member when the extendible rod is at its shortest length. However, the dental brace disclosed in Patent Document 1 is a bulky dental brace due to the nut, which is a separate member, being provided at an outer side.

Moreover, in the dental brace disclosed in Patent Document 2, the bite system is fixed to the maxillary brace and the mandibular brace by fastenings. Thus to separate the maxillary brace and the mandibular brace from each other, there is a need to detach the fastenings by using a dedicated tool or the like to, for example, break the fastenings. Thus time and effort is required when there is a desire to replace the mandibular brace alone.

An object of a first aspect of the present disclosure is accordingly to provide a compact coupling member, and a mouthpiece equipped with such a coupling member.

Moreover, an object of a second aspect of the present disclosure is to provide a mouthpiece that enables easy separation of a maxillary attachment and a mandibular attachment that have been coupled together.

Solution to Problem

The following exemplary embodiments <1> to <10> are examples of the first aspect of the present disclosure.
The following exemplary embodiments <11> to <16> are examples of the second aspect of the present disclosure.

<1> A coupling member includes a sliding member having one axial direction end portion that is configured to be coupled to a first attachment portion provided to a first attachment that is adapted to be mounted to one of a maxilla or a mandible, and a sleeve having one axial direction end portion that is configures to be coupled to a second attachment portion provided to a second attachment that is adapted to be mounted to the other of the maxilla and the mandible. The sliding member is inserted into the sleeve so as to be slidable, and a restricting section is formed at the sleeve between two axial direction end portions of the sleeve so as to restrict sliding of the sliding member in both directions along an axial direction of the sliding member.

According to the above configuration <1>, the coupling member can be made to follow movement of the first attachment and the second attachment by the sliding member sliding inside the sleeve. When this occurs, sliding of the sliding member of the coupling member is restricted in both directions along the axial direction of the sleeve by the restricting section that is formed between the two axial direction end portions of the sleeve.

Due to the sliding member being provided inside the sleeve in such cases, the coupling member can be made more compact than configurations in which engagement members such as nuts are provided at an outer portion of the sleeve. Note that "between two axial direction end portions" in the present disclosure indicates between one axial direction end face of the sleeve and another axial direction end face thereof, namely at an axial direction inner side of the two axial direction end faces of the sleeve.

<2> A coupling member recited in <1>, wherein the first attachment portion is formed projecting out from an outer wall face of the first attachment, the second attachment portion is formed projecting out from an outer wall face of the second attachment, and the sliding member is configured by a rod and a tube shaped engagement member. The rod has one axial direction end portion coupled to the first attachment portion and is formed with a screw portion at another axial direction end portion. The tube shaped engagement member has a screw receiving portion, that is formed at an inner peripheral face of one axial direction end portion of the engagement member, into which the screw portion of the rod is screwed.

According to the above configuration <2>, the length of the coupling member is adjusted by adjusting an amount by which the screw portion of the rod is screwed into the screw receiving portion of the engagement member, thereby enabling the relative position of the first attachment and the second attachment to be adjusted. Moreover, the coupling member can be made to follow movement of the first attachment and the second attachment by the engagement member sliding inside the sleeve.

<3> The coupling member recited in <2>, wherein the restricting section is configured by a slit formed at an outer peripheral face of the sleeve along the axial direction of the sleeve, a projection is formed at an outer peripheral face at another axial direction end portion of the engagement member, and the projection is inserted into the slit.

According to the above configuration <3>, sliding of the engagement member is restricted by the projection formed at the outer peripheral face of the engagement member abutting the two end portions of the slit formed at the outer peripheral face of the sleeve. Due to the projection of the engagement member moving inside the slit of the sleeve, the coupling member can be made to follow movement of the first attachment and the second attachment while also suppressing axial rotation of the engagement member with respect to the sleeve.

<4> The coupling member recited in <3>, wherein a pair of slits are formed at opposing positions at the outer peripheral face of the sleeve.

According to the above configuration <4>, the slits, into which projections of the engagement member are inserted into, are respectively formed at opposing positions at the outer peripheral face of the sleeve. Thus axial rotation of the engagement member with respect to the sleeve can be better suppressed.

<5> The coupling member recited in <2>, wherein the restricting section is configured by a pair of stoppers provided inside the sleeve, and the engagement member is inserted into the sleeve between the pair of stoppers.

According to the above configuration <5>, sliding of the engagement member is restricted in both directions in the axial direction of the engagement member by the stoppers due to the engagement member being inserted between the pair of stoppers provided inside the sleeve. Note that due to the stoppers being provided inside the sleeves, the coupling member can be made more compact than configurations in which stoppers are provided at an outer portion of the sleeve.

<6> The coupling member recited in <2>, wherein the restricting section is configured by narrow diameter portions formed at an inner peripheral face of the sleeve, and a wider diameter portion is formed at the engagement member so as to abut the narrow diameter portion.

According to the above configuration <6>, the narrow diameter portions are formed at the inner peripheral face of the sleeve, and the wider diameter portion is formed at the engagement member. Thus sliding of the engagement member is restricted in both directions in the axial direction of the engagement member by the wider diameter portion of the engagement member abutting the narrow diameter portions of the sleeve. Note that due to the wider diameter portion of the engagement member abutting the narrow diameter portions inside the sleeve, the coupling member can be made more compact than configurations in which the wider diameter portion of the engagement member abuts the sleeve at the outer side of the sleeve.

<7> The coupling member recited in any one of <2>, <5>, or <6>, wherein the engagement member is rotatable around an axis, and an amount that the screw portion of the rod is screwed into the screw receiving portion of the engagement member is adjustable by rotation about the axis of the engagement member.

According to the above configuration <7>, the amount by which the screw portion of the rod is screwed into the screw receiving portion of the engagement member can be adjusted by the rotation around the axis of the engagement member without rotating around an axis of the rod. This enables the length of the coupling member to be adjusted in a state in which one axial direction end portion of the rod is coupled to the first attachment portion.

<8> The coupling member recited in any one of <2>, or <5> to <7>, wherein one axial direction end portion of the sleeve is open, and an insertion space is formed at another axial direction end portion of the engagement member for inserting a tool therein.

According to the above configuration <8>, the engagement member can be rotated around the axis by inserting the tool into the insertion space of the engagement member through the one axial direction end portion of the sleeve and rotating the tool. Since the position of the rod with respect to the engagement member can be adjust without rotating the rod about the axis, the length of the coupling member can be adjusted in a state in which the rod is coupled to the first attachment portion of the first attachment.

<9> The coupling member recited in any one of <2> to <8>, wherein the screw portion of the rod is a male threaded portion having a scale formed thereon, the screw receiving portion of the engagement member is configured by a female threaded portion, and an opening is formed at an outer peripheral face of the engagement member at the one axial direction end portion of the engagement member.

According to the above configuration <9>, the length of the coupling member can be adjusted by adjusting the amount by which the male threaded portion of the rod is screwed into the female threaded portion of the engagement member. Since the scale is formed at the rod and the opening is formed at the outer peripheral face of the one axial direction end portion of the engagement member, the amount by which the male threaded portion is screwed into the female threaded portion can be visually confirmed by looking at the scale through the opening in the engagement member.

<10> A mouthpiece includes the coupling member of any one of <1> to <9>, a mandibular attachment serving as the first attachment, a maxillary attachment serving as the second attachment, the first attachment portion projecting from an outer wall face of the mandibular attachment, and the second attachment portion projecting from an outer wall face of the maxillary attachment.

According to the above configuration <10>, the mouthpiece includes the coupling member of any one of <1> to <9>, namely the coupling member in which sliding of the engagement member, that is inserted inside the sleeve, is restricted by the restricting section formed between the two axial direction end portions of the sleeve. This enables the mouthpiece to be made more compact than configurations which includes a coupling member in which an engagement member such as a nut is provided at an outer portion of the sleeve.

<11> A mouthpiece includes a maxillary attachment that is mounted to a maxilla, a mandibular attachment that is mounted to a mandible, an upper attachment portion provided at the maxillary attachment, a lower attachment portion provided at the mandibular attachment, and a coupling member. The coupling member is attached to the upper attachment portion and the lower attachment portion. At an attachment angle of the coupling member in a mounted state of the maxillary attachment and the mandibular attachment to the maxilla and the mandible, the coupling member is suppressed from attaching to or detaching from the upper attachment portion and the lower attachment portion. At an attachment angle of the coupling member in a non-mounted state of the maxillary attachment and the mandibular attachment to the maxilla and the mandible, the coupling member is attached to or detached from at least one of the upper attachment portion or the lower attachment portion.

According to the above configuration <11>, the coupling member is attachable to or detachable from at least one of the upper attachment portion or the lower attachment portion at an attachment angle of the coupling member in the non-mounted state of the maxillary attachment and the mandibular attachment to the maxilla and the mandible. Accordingly, the maxillary attachment and the mandibular attachment can be easily separated from each other.

However, attachment and detachment of the coupling member to the upper attachment portion and the lower attachment portion is suppressed at an attachment angle of the coupling member in the mounted state of the maxillary attachment and the mandibular attachment to the maxillary and the mandible. Accordingly, the coupled state can be maintained between the maxillary attachment and the mandibular attachment.

<12> The mouthpiece recited in <11>, wherein the upper attachment portion is formed projecting out from an outer wall face of the maxillary attachment, and the lower attachment portion is formed projecting out from an outer wall face of the mandibular attachment.

According to the above configuration <12>, the coupling member is easily attached to the upper attachment portion and the lower attachment portion due to the upper attachment portion and the lower attachment portion being formed respectively projecting out from the outer wall face of the maxillary attachment and the mandibular attachment. Moreover, when the coupling member is attached to the upper attachment portion and the lower attachment portion, movement of the tongue can be suppressed from being impeded by the coupling member better than in configurations in which the upper attachment portion and the lower attachment portion are provided at the inner wall faces or the like of the maxillary attachment and the mandibular attachment.

<13> The mouthpiece recited in <11> or <12>, wherein at least one of the upper attachment portion or the lower attachment portion includes a shaft portion provided with a flange portion having a long axis and a short axis and provided in a vicinity of a leading end of the shaft portion. The coupling member includes an eyelet portion that is engaged with the flange portion. The eyelet portion has a major diameter that is longer than a length of the long axis of the flange portion and has a minor diameter that is longer than a length of a short axis of the flange portion and shorter than the length of the long axis of the flange portion.

According to the above configuration <13>, the flange portion having the long axis and the short axis is provided at at least one of the upper attachment portion or the lower attachment portion. The major diameter of the eyelet portion of the coupling member is longer than the length of the long axis of the flange portion. The minor diameter of the coupling member is longer than the length of the short axis of the flange portion and shorter than the length of the long axis of the flange portion.

Thus the coupling member can be made attachable and detachable, or attaching and detaching of the coupling member can be suppressed, by changing an attachment angle of the coupling member with respect to the mouthpiece, namely by changing the attachment angle of the eyelet portion with respect to the flange portion.

<14> The mouthpiece recited in <13>, wherein the flange portion is able to pass through the eyelet portion when a long axis direction of the flange portion is aligned with a major diameter direction of the eyelet portion.

According to the above configuration <14>, the flange portion is able to pass through the eyelet portion when the long axis direction of the flange portion is aligned with the major diameter direction of the eyelet portion. Thus the eyelet portion of the coupling member can be removed from the flange portion of the upper attachment portion or the lower attachment portion by aligning the major diameter direction of the eyelet portion with the long axis direction of the flange portion in a non-mounted state of the maxillary attachment and the mandibular attachment to the maxillary and the mandible.

However, the eyelet portion is rendered substantially irremovable from the flange portion by ensuring the long axis direction of the flange portion and the major diameter direction of the eyelet portion are not aligned in a mounted state of the maxillary attachment and the mandibular attachment to the maxillary and the mandible. This enables the coupled state between the maxillary attachment and the mandibular attachment to be maintained.

<15> The mouthpiece recited in <13> or <14>, wherein the flange portion has a shape similar to a shape of the eyelet portion.

According to the above configuration <15>, due to the flange portion having a shape similar to a shape of the eyelet portion, the flange portion is able to pass through the eyelet portion by positioning the angle of the flange portion and the angle of the eyelet portion so as to be substantially aligned with each other. However, the flange portion is substantially unable to pass through the eyelet portion when the angle of the flange portion and the angle of the eyelet portion are not aligned with each other.

<16> The mouthpiece recited in <15> wherein the flange portion and the eyelet portion are formed with ellipsoidal shapes.

According to the above configuration <16>, the flange portion and the eyelet portion are formed with ellipsoidal shapes. Thus the coupling member can be made attachable and detachable, or attaching and detaching of the coupling member can be suppressed, without making the flange portion and the eyelet portion in a complicated shape.

<17> The mouthpiece recited in any one of <13> to <16>, wherein a major diameter direction of the eyelet portion is configured along a length direction of the coupling member, and an angle of the long axis of the flange portion with respect to an opposing face of the maxillary attachment, opposing the mandibular attachment, or with respect to an opposing face of the mandibular attachment, opposing the maxillary attachment, is outside of a range of from 10 degrees to 60 degrees.

According to the above configuration <17>, the attachment angle of the coupling member to the upper attachment portion or the lower attachment portion (the angle of the major diameter of the eyelet portion) is from about 10 degrees to about 60 degrees in a mounted state of the maxillary attachment and the mandibular attachment to the maxillary and the mandible. Thus, due to the angle of the long axis of the flange portion with respect to the opposing face of the mandibular attachment or the maxillary attachment is outside the range of from about 10 degrees to about 60 degrees, the eyelet portion can be prevented from coming off the flange portion in the mounted state of the maxillary attachment and the mandibular attachment to the maxillary and the mandible.

Advantageous Effects

The first aspect enables provision of a compact coupling member, and a mouthpiece including a compact coupling member.

The second aspect enables provision of a mouthpiece in which a maxillary attachment and a mandibular attachment that have been coupled together can be easily separate from each other.

BRIEF DESCRIPTION OF DRAWINGS

FIG. 7A is a front view illustrating a coupling member of a mouthpiece according to the fifth exemplary embodiment of the first aspect in an extended state.

FIG. 7B is a plan view illustrating a coupling member of a mouthpiece according to the fifth exemplary embodiment of the first aspect in an extended state.

FIG. 7C is a cross-section taken on line E-E of FIG. 7A.

FIG. 7E is a bottom view illustrating a coupling member of a mouthpiece according to the fifth exemplary embodiment of the first aspect in an extended state.

DESCRIPTION OF EMBODIMENTS

Figure 1:
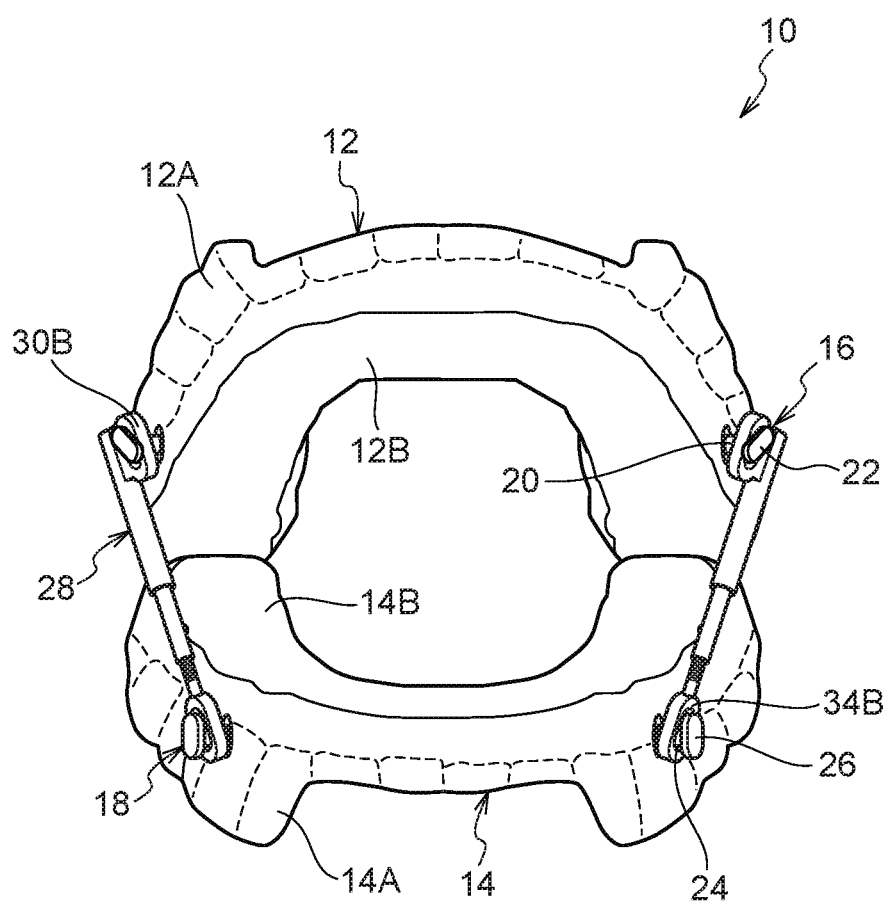
FIG. 1 is a front view illustrating a mouthpiece according to a first exemplary embodiment of a first aspect.

In the present specification "a posterior side" indicates a back teeth (for example, tooth positions 4 to 8) side when the mouthpiece is being worn, namely, the palatal side. Moreover, "left and right sides" indicates the left and right sides when looking face-on to a center of dentition, namely tooth position 1.

Explanation follows regarding examples of a first aspect and a second aspect of the present disclosure, with reference to the drawings. However, the present disclosure is not limited to the aspects illustrated in the drawings. Note that sizes of members in each of the drawings are only schematic, and relative size relationships between members are not limited thereto.

First Aspect A coupling member according to a first aspect of the present disclosure includes a sliding member having one axial direction end portion coupled to a first attachment portion, that is provided at a first attachment that is mounted to one of a maxilla or a mandible, and a sleeve having one axial direction end portion coupled to a second attachment portion, that is provided at a second attachment that is mounted to the other of the maxilla and the mandible. The sliding member is inserted into the sleeve so as to be capable of sliding, and a restricting section is formed at the sleeve between two axial direction end portions of the sleeve so as to restrict the sliding member from sliding in both directions along an axial direction of the sleeve.

According to the first aspect, due to the sliding member of the coupling member being provided inside the sleeve, the coupling member can be made more compact than configurations in which an engagement member such as a nut is provided at an outer portion of the sleeve.

First Exemplary Embodiment

Explanation follows regarding a mouthpiece according to a first exemplary embodiment of the first aspect, with reference to FIG. 1 to FIG. 3C.

Mouthpiece

A mouthpiece 10 of the present exemplary embodiment is, for example, a mouthpiece employed for sleep apnea syndrome that is utilized to reduce or prevent snoring and bruxism, and breathing interruptions or the like while sleeping. As illustrated in FIG. 1, the mouthpiece 10 includes a maxillary attachment 12 (an example of a second attachment) that is mounted to maxillary dentition, and a mandibular attachment 14 (an example of a first attachment) that is mounted to mandibular dentition.

The maxillary attachment 12 and the mandibular attachment 14 are, for example, configured from an acrylic resin. However, they may be configured from a single hard material having a bending elastic modulus of from 2000 MPa to 3000 MPa. or from a combination of materials combining a soft material having a bending elastic modulus of from 10 MPa to 300 MPa, and a hard material having a bending elastic modulus of from 1000 MPa to 3000 MPa.

Note that the maxillary attachment 12 and the mandibular attachment 14 may be configured from a comparatively soft material having a tensile strength of 150 N or greater but less than 2000 N, or in particular from 150 N to 500 N. In such cases, the maxillary attachment 12 and the mandibular attachment 14 have a high ability to conform to the teeth when the mouthpiece 10 is being worn.

Note that tensile strength refers to a breaking strength when a stretch test is performed in the direction of the molars (namely, the posterior direction in the dentition) with a hole of 1.5 mm diameter opened at tooth position 6 of the maxillary attachment of a mouthpiece (of thickness 3 mm) manufactured using a Nissin standard model.

Examples of materials having a tensile strength of 150 N or greater but less than 2000 N include olefin-based resins, polyester-based resins, urethane-based resins, polyamide-based resins, and acrylic-based rubber resins, and among these olefin-based resins are preferable.

Olefin-based resins are polymers produced by polymerizing a single olefin, or copolymers produced by polymerizing an olefin with another monomer. Such olefins are preferably olefins with 2 to 6 carbons such as, for example, ethylene, propylene, butene, methylpentene, and hexane. Examples of other monomers include vinyl acetate.

Preferable examples of olefin-based resins include polyethylene (PE), polyethylene-based resins, polypropylene (PP), polypropylene-based resins, ethylene-vinyl acetate copolymers (EVA). Polyethylene (PE), polyethylene-based resins, polypropylene (PP), and polypropylene-based resins are particularly preferable.

Examples of polyester-based resins include condensation polymers of a polyvalent carboxylic acid (dicarboxylic acid) and a polyalcohol (diol), and a specific example thereof is polyethylene terephthalate (PET). Moreover, examples of urethane-based resins include condensation polymers of a compound including an isocyanate group and a compound including a hydroxide group, such as a thermoplastic polyurethane (TPU).

Examples of polyamide-based resins include polymers of plural monomers bonded together by amide bonds, such as NYLON, para-amides, and meta-amides. Moreover, acrylic-based rubber resins are resins in which a main component is an acrylic-based rubber, and examples thereof include block-copolymers of methyl methacrylate and butyl acrylate.

Commercially available materials may be employed as the material having a tensile strength of 150 N or greater but less than 2000 N, and, for example, F327 or the like manufactured by Prime Polymer Co., Ltd. may be employed as a polypropylene resin.

Metal upper attachment portions 16 (examples of second attachment portions) are provided at an outer wall face 12A at left and right posterior sides of the maxillary attachment 12 (at tooth positions 6 to 7 in the present exemplary embodiment) as viewed from the center of dentition, so as to project out from the outer wall face 12A.

Metal lower attachment portions 18 (examples of first attachment portions) are provided at an outer wall face 14A at left and right posterior sides of the mandibular attachment 14 (at tooth positions 3 to 4 in the present exemplary embodiment) as viewed from the center of dentition, so as to project out from the outer wall face 14A.

The upper attachment portions 16 each includes a circular bar shaped shaft portion 20 having one end fixed to the outer wall face 12A of the maxillary attachment 12, and a flange portion 22 provided at the other end (leading end) of the shaft portion 20. Note that the flange portion 22 has an ellipsoidal shape with a long axis and a short axis. Moreover, as illustrated in FIG. 3B, an angle of the long axis of the flange portion 22 with respect to an opposing face 12B of the maxillary attachment 12 opposing the mandibular attachment 14 is about 90 degrees.

Similarly, the lower attachment portion 18 includes a shaft portion 24, and an ellipsoidal shaped flange portion 26 provided at a leading end of the shaft portion 24. Moreover, as illustrated in FIG. 3B, an angle of the long axis of the flange portion 26 with respect to an opposing face 14B of the mandibular attachment 14 opposing the maxillary attachment 12 is about 90 degrees. Note that the angles of the long axes of the flange portions 22, 26 with respect to the opposing faces 12B, 14B may be set anywhere outside of a range of from 10 degrees to 60 degrees.

Moreover, the right upper attachment portion 16 and the right lower attachment portion 18, and the left upper attachment portion 16 and the left lower attachment portion 18, are coupled together by respective metal coupling members 28 so that the coupling members 28 are rotatable about the axes of the upper attachment portions 16 and the lower attachment portions 18. The coupling members 28 couple the maxillary attachment 12 and the mandibular attachment 14 together to enable opening and closing, and also position the mandibular attachment 14 so that movement in a posterior side of the dentition does not occur with respect to the maxillary attachment 12.

In the mouthpiece 10 of the present exemplary embodiment, the upper attachment portions 16 are disposed at a posterior side to (at a back teeth side of) the lower attachment portions 18 as viewed from the center of dentition. Namely, the mouthpiece 10 is a push-type mouthpiece that, when being worn, pushes the mandibular attachment 14 (the mandible) forward using the coupling members 28.

Coupling Members

Figure 2A:
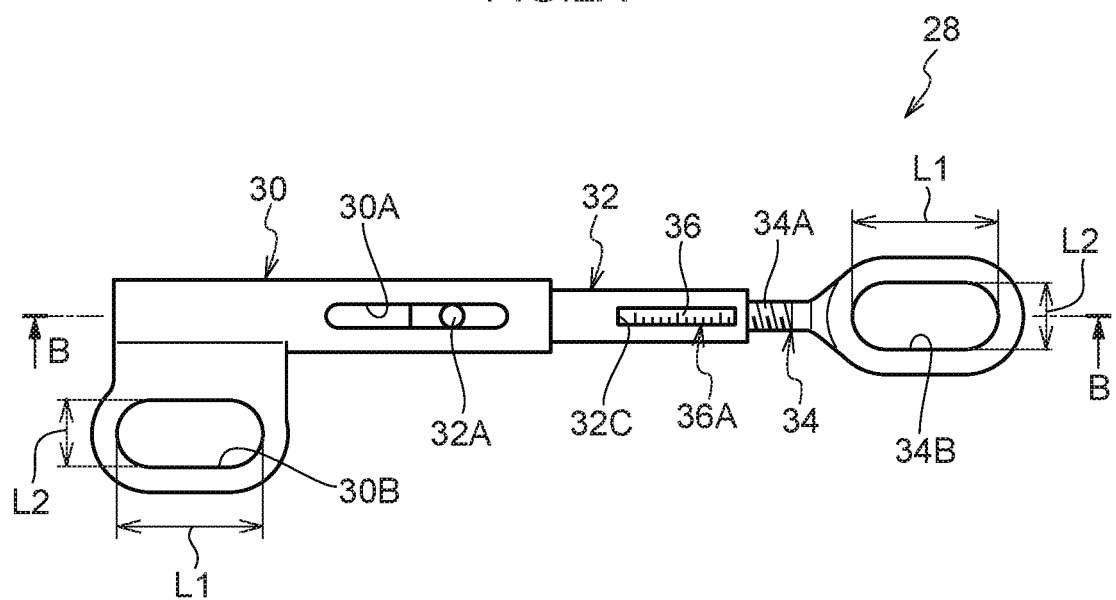
FIG. 2A is a plan view illustrating a coupling member of a mouthpiece according to the first exemplary embodiment of the first aspect.
Figure 2B:
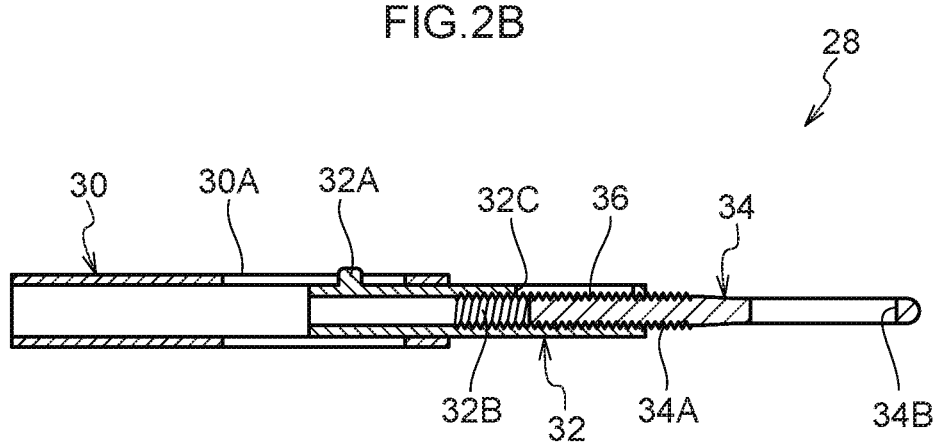
FIG. 2B is a cross-section taken on line B-B of FIG. 2A.

As illustrated in FIG. 2A and FIG. 2B, the coupling members 28 each includes a tube shaped sleeve 30 that is open at both axial direction end portions, a tube shaped engagement member 32 provided so as to be slidable inside the sleeve 30, and a rod 34 engaged with the engagement member 32. Note that a sliding member is configured by the engagement member 32 and the rod 34.

A slit 30A (an example of a restricting section) is formed along the axial direction at an outer peripheral face of the sleeve 30 between the two axial direction end portions of the sleeve 30. An ellipsoidal shaped upper eyelet portion 30B is formed at the sleeve 30 at a position offset from the axial center of an axial direction upper end portion (left end portion in FIG. 2A) of the sleeve 30. The upper eyelet portion 30B engages with the flange portion 22 of the upper attachment portions 16 of FIG. 1.

The upper eyelet portion 30B has a major diameter direction oriented in the same direction as the length direction of the coupling member 28 (namely, the axial direction of the sleeve 30), has a size that is slightly larger than the flange portion 22, and has a shape similar to that of the flange portion 22. Specifically, a major diameter length L1 of the upper eyelet portion 30B is longer than a long axis length R1 of the flange portion 22 illustrated in FIG. 3B.

A minor diameter length L2 of the upper eyelet portion 30B is longer than a short axis length R2 of the flange portion 22 illustrated in FIG. 3B, and is shorter than the long axis length R1 of the flange portion 22. Thus the upper eyelet portion 30B is attachable to or detachable from the flange portion 22 only when positioned such that the major diameter direction of the upper eyelet portion 30B is aligned with the long axis direction of the flange portion 22.

A projection 32A is formed so as to project out from an outer peripheral face at an axial direction upper end portion (left end portion in FIG. 2A) of the engagement member 32. The projection 32A has a diameter slightly smaller than a width of the slit 30A of the sleeve 30, and is inserted so as to be capable of sliding inside the slit 30A. Moreover, a female threaded portion 32B is formed on an inner peripheral face of an axial direction lower end portion (the right end portion in FIG. 2B) of the engagement member 32, and an opening 32C is formed at the outer peripheral face of the engagement member 32 at the axial direction lower end portion thereof.

A male threaded portion 34A is formed at an axial direction upper end portion (left end portion in FIG. 2A) of the rod 34, and the male threaded portion 34A is screwed into the female threaded portion 32B of the engagement member 32. A thread-free portion 36 is provided at a portion along the axial direction of the male threaded portion 34A, and a scale 36A is formed at the thread-free portion 36.

An ellipsoidal shaped lower eyelet portion 34B is formed at an axial direction lower end portion (right end portion in FIG. 2A) of the rod 34. The lower eyelet portion 34B engages with the flange portion 26 of the lower attachment portions 18 illustrated in FIG. 1. The lower eyelet portion 34B is, for example, formed at the center axis of the rod 34, with a major diameter direction oriented in the same direction as the length direction of the coupling member 28 (namely, as the axial direction of the rod 34).

Moreover, similarly to the upper eyelet portion 30B, the lower eyelet portion 34B has a size that is slightly larger than the flange portion 26, and has a shape similar to that of the flange portion 26. Specifically, a major diameter length L1 of the lower eyelet portion 34B is longer than a long axis length R1 of the flange portion 26 illustrated in FIG. 3B.

Moreover, a minor diameter length L2 of the lower eyelet portion 34B is longer than a short axis length R2 of the flange portion 26 illustrated in FIG. 3B, and shorter than the long axis length R1 of the flange portion 26. Thus the lower eyelet portion 34B is attachable to or detachable from the flange portion 26 only when positioned such that the major diameter direction of the lower eyelet portion 34B is aligned with the long axis direction of the flange portion 26.

The coupling member 28 has a length that is adjustable in a continuous manner by axially rotating the rod 34 to adjust the amount of the male threaded portion 34A screwed into the female threaded portion 32B of the engagement member 32. Moreover, the coupling member 28 follows movement of the maxillary attachment 12 and the mandibular attachment 14 by the engagement member 32 sliding inside the sleeve 30.

When this occurs, the engagement members 32 are restricted from sliding in both directions along the axial direction of the engagement members 32 by the projections 32A of the respective engagement members 32 abutting the two end portions (left and right end portions in FIG. 2A) of the slits 30A of the sleeves 30. Note that respective distances (distances between centers) between the upper attachment portions 16 and the lower attachment portions 18 are adjustable using the coupling members 28 over a range from about 18 mm to about 50 mm.

Operation and Advantageous Effects

As illustrated in FIG. 1, the mouthpiece 10 is mounted to dentition in a state in which the maxillary attachment 12 and the mandibular attachment 14 are coupled together by the coupling members 28 by hooking the upper eyelet portions 30B onto the shaft portions 20 and hooking the lower eyelet portions 34B onto the shaft portions 24.

The position of the mandibular attachment 14 is adjusted in this state by adjusting the amount of the male threaded portion 34A of FIG. 2A and FIG. 2B screwed into the female threaded portion 32B, such that the mandibular attachment 14 is positioned so that movement to the posterior side of the dentition does not occur with respect to the maxillary attachment 12. Note the amount by which the male threaded portion 34A is screwed in is confirmed by looking at the scale 36A formed at the thread-free portion 36 of the rod 34 through the opening 32C of the engagement member 32.

Figure 3A:
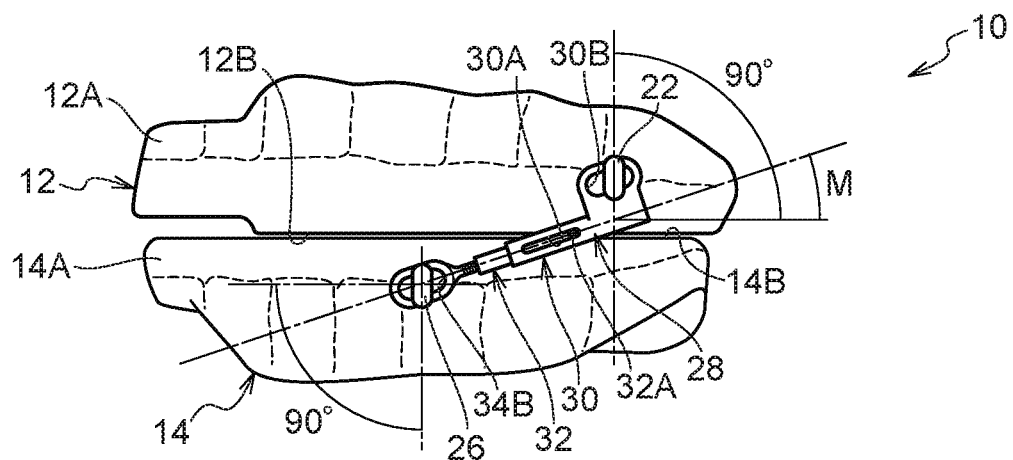
FIG. 3A is a side view illustrating a mouthpiece according to the first exemplary embodiment of the first aspect in a closed state.
Figure 3B:
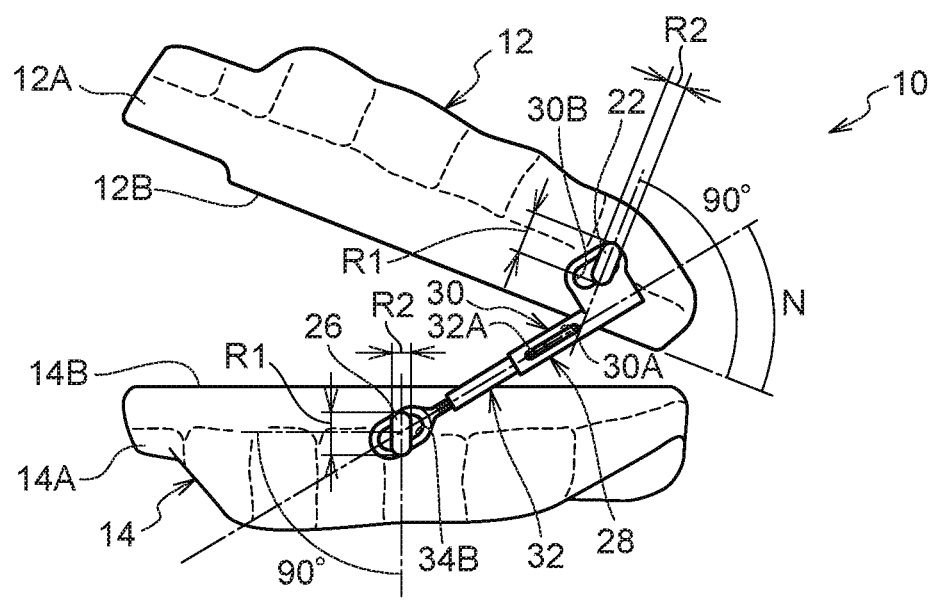
FIG. 3B is a side view illustrating a mouthpiece according to the first exemplary embodiment of the first aspect in an open state.

In a closed mouth state, as illustrated in FIG. 3A, posterior side movement (toward the right in FIG. 3A) of the mandibular attachment 14 is restricted by the projection 32A of the engagement member 32 abutting the upper end portion (the right end portion in FIG. 3A) of the slit 30A of the sleeve 30.

Moreover, in a closed mouth state, the attachment angle M of the coupling member 28, namely, the angle of the major diameter of the upper eyelet portion 30B with respect to the opposing face 12B of the maxillary attachment 12, and the angle of the major diameter of the lower eyelet portion 34B with respect to the opposing face 14B of the mandibular attachment 14, are about 10 degrees.

Due to the respective angles of the long axes of the flange portions 22, 26 to the opposing face 12B or the opposing face 14B being about 90 degrees in this state, the angles of the long axes of the flange portions 22, 26 are not aligned with the angles of the major diameters of the upper eyelet portion 30B and the lower eyelet portion 34B.

Thus in a closed mouth state, the flange portions 22, 26 are substantially unable to pass through the upper eyelet portion 30B and the lower eyelet portion 34B. Namely, the coupling members 28 are substantially irremovable from the upper attachment portions 16 and the lower attachment portions 18, maintaining the coupled state between the maxillary attachment 12 and the mandibular attachment 14.

Similarly, in an open mouth state, as illustrated in FIG. 3B, an attachment angle N of the coupling member 28, namely, an angle of the major diameter of the upper eyelet portion 30B to the opposing face 12B of the maxillary attachment 12, and an angle of the major diameter of the lower eyelet portion 34B to the opposing face 14B of the mandibular attachment 14, is from about 40 degrees to about 60 degrees.

Due to the respective angles of the long axes of the flange portions 22, 26 to the opposing face 12B or the opposing face 14B being about 90 degrees, the angles of the long axes of the flange portions 22, 26 are not aligned with the angles of the major diameters of the upper eyelet portion 30B and the lower eyelet portion 34B.

Thus in an open mouth state, the flange portions 22, 26 are substantially unable to pass through the upper eyelet portion 30B and the lower eyelet portion 34B. Namely, the coupling members 28 are substantially irremovable from the upper attachment portions 16 and the lower attachment portions 18, maintaining the coupled state between the maxillary attachment 12 and the mandibular attachment 14.

Note that in an open mouth state, the coupling members 28 follow movement of the maxillary attachment 12 and the mandibular attachment 14 by the engagement members 32 sliding inside the sleeves 30. When this occurs, the projections 32A of the engagement members 32 move downward (toward the left in FIG. 3B) from an upper end portion of the slit 30A of the sleeve 30 and abut a lower end portion (left end portion in FIG. 3B) of the slit 30A.

Figure 3C:
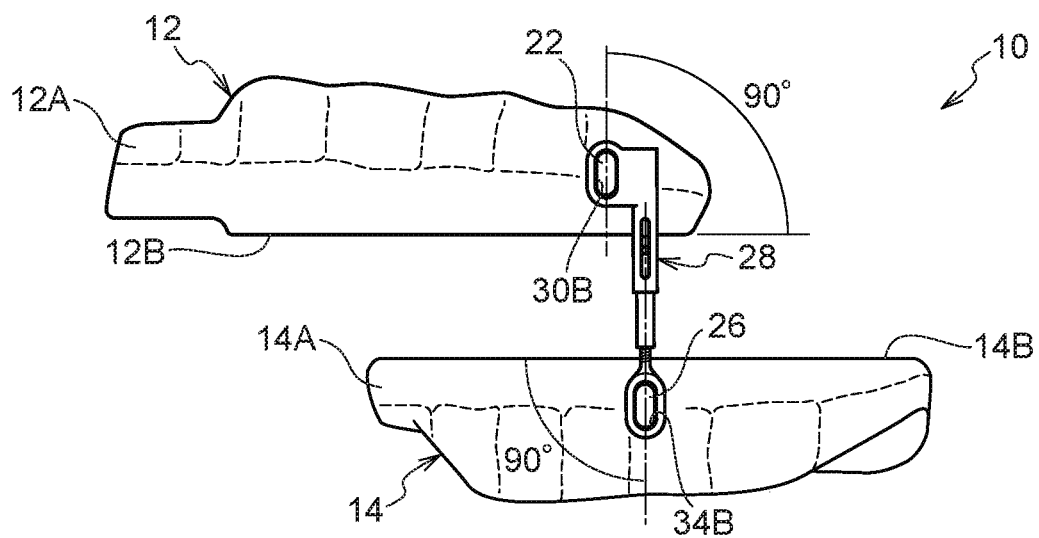
FIG. 3C is a side view illustrating a coupling member of a mouthpiece according to the first exemplary embodiment of the first aspect during detaching.

In order to attach or detach the coupling members 28 to or from the maxillary attachment 12 and the mandibular attachment 14 (to or from the upper attachment portions 16 and the lower attachment portions 18), first the mouthpiece 10 is removed from the dentition. Then, as illustrated in FIG. 3C, the maxillary attachment 12 and the mandibular attachment 14 are separated from each other so as to lie in a substantially horizontal direction such that the attachment angles of the coupling members 28 are about 90 degrees.

When this is performed, the angle of the major diameter of the upper eyelet portion 30B to the opposing face 12B of the maxillary attachment 12, and the angle of the major diameter of the lower eyelet portion 34B to the opposing face 14B of the mandibular attachment 14, also become about 90 degrees.

Namely, the angles of the long axes of the flange portions 22, 26 and the angles of the major diameters of the upper eyelet portion 30B and the lower eyelet portion 34B are aligned with each other, and the flange portions 22, 26 are able to pass through the upper eyelet portion 30B and the lower eyelet portion 34B. This enables the coupling members 28 to be removed from the upper attachment portions 16 and the lower attachment portions 18.

In the present exemplary embodiment, the amount by which the male threaded portion 34A is screwed into the female threaded portion 32B is adjusted by axially rotating the rod 34. The rods 34 are substantially non-axially-rotatable in a state in which the lower eyelet portion 34B is engaged with the flange portion 26. Thus the rods 34 can be prevented from unintentionally rotating and changing the length of the coupling members 28 while the mouthpiece 10 is being worn on the dentition.

Moreover, in the present exemplary embodiment the engagement members 32 are restricted from sliding in both directions along the axial direction of the engagement members 32 by the projections 32A of the engagement members 32, that are provided inside the respective sleeves 3, abutting the two end portions of the slits 30A formed between the two axial direction end portions of the sleeves 30.

This enables the coupling members 28 and the mouthpiece 10 to be made more compact than configurations in which engagement members such as nuts are provided at outer portions of the sleeves 30, or the engagement members 32 and the rods 34 abut at outside end portions of the sleeves 30.

Note that the projections 32A of the engagement members 32 move along the axial direction inside the slits 30A of the sleeves 30. Thus when the engagement members 32 are sliding inside the sleeves 30, the engagement members 32 can be suppressed from axially rotating with respect to the sleeves 30.

Moreover, in the present exemplary embodiment, the scales 36A formed at the thread-free portions 36 of the rods 34 are visible through the openings 32C of the engagement members 32. This enables the amount that the male threaded portions 34A have been screwed in to be confirmed while the male threaded portions 34A of the rods 34 have been screwed into the female threaded portions 32B of the engagement members 32.

Moreover, in the present exemplary embodiment, the ellipsoidal shaped flange portions 22, 26 are provided at the upper attachment portions 16 and the lower attachment portions 18, and the upper eyelet portions 30B and the lower eyelet portions 34B of the coupling members 28 are formed with ellipsoidal shapes that are slightly larger than those of the flange portions 22, 26 (namely, are formed in similar shapes thereto).

Furthermore, the angles of the long axes of the flange portions 22, 26 to the opposing faces 12B, 14B of the maxillary attachment 12 or the mandibular attachment 14 are about 90 degrees, i.e. lie outside the attachment angle range of the coupling members 28.

This means that in a mounted state of the mouthpiece 10 to dentition, the upper eyelet portions 30B and the lower eyelet portions 34B are suppressed such that the upper eyelet portions 30B and the lower eyelet portions 34B are substantially unable to be attached to or detached from the flange portions 22, 26. This enables the coupled state between the maxillary attachment 12 and the mandibular attachment 14 to be maintained.

Moreover, in a non-mounted state of the mouthpiece 10 to the dentition, the upper eyelet portion 30B of the lower eyelet portion 34B are easily attachable to or detachable from the flange portions 22, 26. In other words, the coupling members 28 can be easily switched between an attachable-detachable state and an attachment-detachment suppressed state by changing the attachment angle of the coupling members 28 with respect to the mouthpiece 10.

Thus the maxillary attachment 12 and the mandibular attachment 14 can be more easily separated than configurations such as those in which the upper eyelet portion 30B and the lower eyelet portion 34B are bonded or screwed to the flange portions 22, 26. This thereby enables maintenance and replacement thereof.

Moreover, due to the upper eyelet portion 30B and the lower eyelet portion 34B being ellipsoidal shaped, when the mouthpiece 10 is being worn at the dentition, gaps are formed between the shaft portions 20 of the upper attachment portions 16 and the upper eyelet portion 30B, and between the shaft portions 24 of the lower attachment portions 18 and the lower eyelet portions 34B. This enables the coupling members 28 to more readily follow movements of the maxillary attachment 12 and the mandibular attachment 14 by the shaft portions 20, 24 sliding in these gaps.

Second Exemplary Embodiment

Figure 4A:
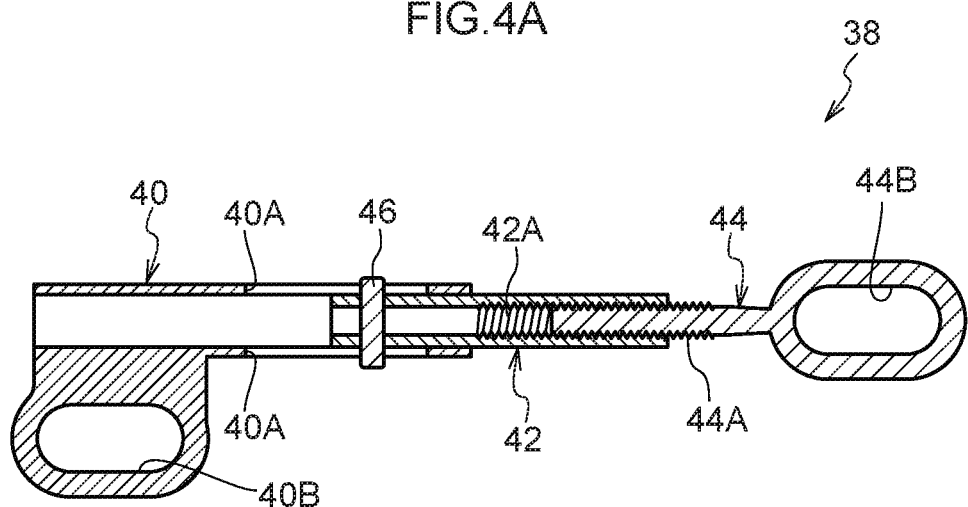
FIG. 4A is a cross-section illustrating a coupling member of a mouthpiece according to a second exemplary embodiment of the first aspect.

Next, explanation follows regarding coupling members 38 of a mouthpiece according to a second exemplary embodiment of the first aspect, with reference to FIG. 4A. Note that explanation will be omitted of configuration similar to that of the coupling members 28 of the first exemplary embodiment.

As illustrated in FIG. 4A, each of the coupling members 38 includes a tube shaped sleeve 40 that is open at both axial direction end portions, a tube shaped engagement member 42 provided so as to be slidable inside the sleeve 40, and a rod 44 engaged with the engagement member 42. Note that a sliding member is configured by the engagement member 42 and the rod 44.

A pair of slits 40A (an example of a restricting section) is formed at an outer peripheral face of each of the sleeves 40 between the two axial direction end portions thereof. The pair of slits 40A are each formed along the axial direction of the sleeves 40 at positions opposing each other. A circular pillar shaped pin 46 is attached to an axial direction upper end portion (left end portion in FIG. 4A) of each of the engagement members 42 so as to pass through the engagement member 42 along a radial direction thereof.

A diameter of the pins 46 is slightly smaller than the width of the slits 40A of the sleeves 40. Two end portions of the pins 46 project out from the outer peripheral faces of the engagement members 42, and are inserted inside the pairs of slits 40A so as to be capable of sliding along the slits 40A.

The coupling members 38 have lengths that are variable by the engagement members 42 sliding inside the sleeves 40. When this occurs, sliding of the engagement members 42 is restricted in both directions along the axial direction of the engagement members 42 by the pins 46, attached to the engagement members 42, abutting the two end portions of the slits 40A of the sleeves 40 (the left and right end portions in FIG. 4A).

In the present exemplary embodiment, sliding of the engagement members 42 inside the sleeves 40 are restricted in both directions along the axial direction thereof by the pins 46, attached to the engagement members 42, abutting the two end portions of the slits 40A formed between the two axial direction end portions of the sleeves 40. Thus the coupling members 38 can be made more compact than configurations in which engagement members such as nuts are provided at outer sides of the sleeves 40, or the engagement members 42 and the rods 44 respectively abut at outer side end portions of the sleeves 40.

Moreover, due to the two end portions of the pins 46 being respectively inserted into the pair of slits 40A, provided at the outer peripheral face of each of the sleeves 40, the engagement members 42 can be suppressed from axially rotating with respect to the sleeves 40 when the engagement members 42 are sliding inside the sleeves 40.

Third Exemplary Embodiment

Figure 4B:
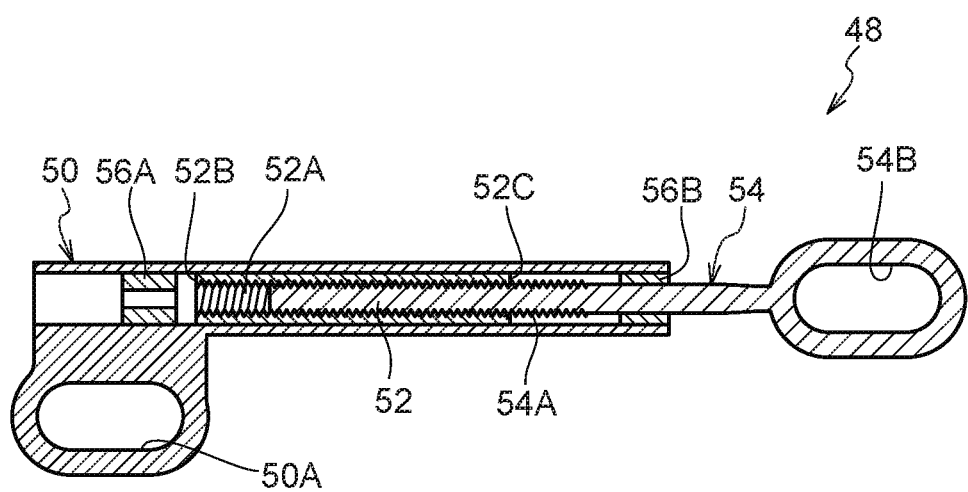
FIG. 4B is a cross-section illustrating a coupling member of a mouthpiece according to a third exemplary embodiment of the first aspect.

Next, explanation follows regarding coupling members 48 of a mouthpiece according to a third exemplary embodiment of the first aspect, with reference to FIG. 4B. Note that explanation will be omitted of configuration similar to that of the coupling members 28, 38 of the first and second exemplary embodiments.

As illustrated in FIG. 4B, the coupling members 48 each includes a tube shaped sleeve 50 that is open at both axial direction end portions, a tube shaped engagement member 52 provided so as to be slidable inside the sleeve 50, and a rod 54 engaged with the engagement member 52. Note that a sliding member is configured by the engagement member 52 and the rod 54.

A pair of stoppers 56A, 56B (an example of a restricting section) is provided between the two axial direction end portions inside each of the sleeves 50. The stoppers 56A, 56B are each, for example, configured with a circular cylinder shape including a hollow portion, and are fixed to an inner peripheral face of the sleeve 50. Note that the shape of the stoppers 56A, 56B is not limited to being a circular cylinder shape, and may be any shape capable of abutting against abutting portions 52B, 52C of the engagement members 52, described later.

An axial direction length of each of the engagement members 52 is shorter than a length between the stoppers 56A, 56B, namely, shorter than a length from a lower end portion of the stopper 56A at the upper end portion side (the left end portion side in FIG. 4B) to an upper end portion of the stopper 56B at the lower end portion side (the right end portion side in FIG. 4B). The engagement members 52 are each inserted inside the respective sleeve 50 between the stoppers 56A, 56B.

Note that the axial direction upper end portion of the engagement member 52 configures the abutting portion 52B that abuts the lower end portion of the stopper 56A, and the axial direction lower end portion of the engagement member 52 configures the abutting portion 52C that abuts the upper end portion of the stopper 56B.

Moreover, a lower eyelet portion 54B at the axial direction lower end portion (right end portion in FIG. 4B) of each of the rods 54 is exposed from the sleeve 50. A male threaded portion 54A at an axial direction upper end portion (left end portion in FIG. 4B) of the rod 54 is inserted through the hollow portion of the stopper 56B into the sleeve 50, and is screwed into a female threaded portion 52A of the engagement member 52.

The coupling members 48 each has a length that is variable by the engagement members 52 sliding inside the sleeves 50 between the stoppers 56A, 56B. When this occurs, sliding of the engagement members 52 are restricted in both directions along the axial direction of the engagement members 52 by the abutting portions 52B, 52C of each of the engagement members 52 respectively abutting the stoppers 56A, 56B.

According to the present exemplary embodiment, sliding of the engagement members 52 inside the sleeves 50 are restricted in both directions along the axial direction of the engagement members 52 by the stoppers 56A, 56B that are provided between the two axial direction end portions provided inside the sleeves 50. This enables the coupling members 48 to be made more compact than configurations in which engagement members and stoppers are provided at outer sides of the sleeves 50.

Fourth Exemplary Embodiment

Figure 5:
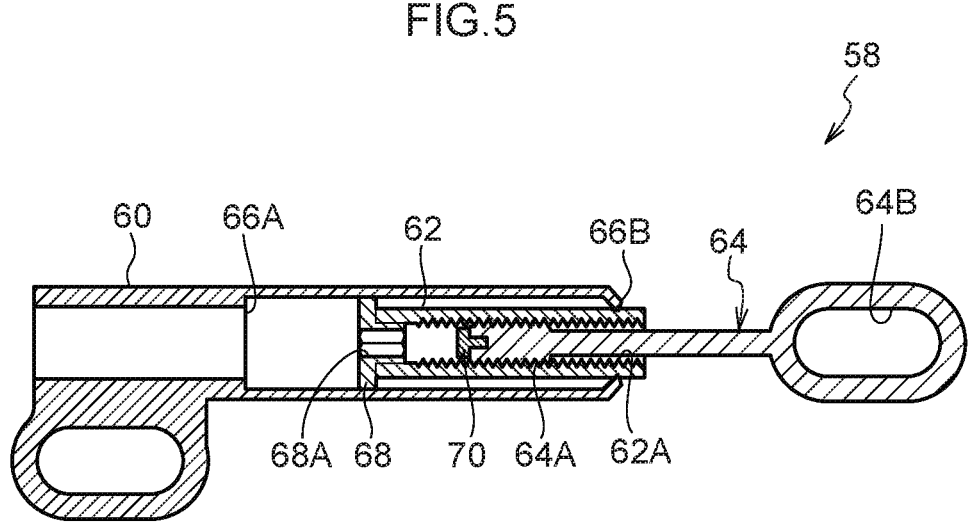
FIG. 5 is a cross-section illustrating a coupling member of a mouthpiece according to a fourth exemplary embodiment of the first aspect.

Explanation follows regarding coupling members 58 of a mouthpiece according to a fourth exemplary embodiment of the first aspect, with reference to FIG. 5. Note that explanation will be omitted of configuration similar to that of the coupling members 28, 38, 48 of the first to third exemplary embodiments.

As illustrated in FIG. 5, the coupling members 58 each includes a tube shaped sleeve 60 that is open at both axial direction end portions, a tube shaped engagement member 62 provided so as to be slidable inside the sleeve 60, and a rod 64 engaged with the engagement member 62. Note that a sliding member is configured by the engagement member 62 and the rod 64.

Narrow diameter portions 66A, 66B (an example of a restricting section) that have smaller internal diameters than internal diameters of other portions of each of the sleeves 60 are formed at inner peripheral faces of the sleeves 60 between the two axial direction end portions thereof. Note that the narrow diameter portion 66A formed further to a lower end side (left end portion side in FIG. 5) from an axial direction upper end face of each of the sleeves 60 is formed by increasing a thickness of wall of the sleeve 60, and the narrow diameter portion 66B formed at an upper end side (right end portion side in FIG. 5) of the axial direction lower end face of the sleeve 60 is formed by crimping a lower end portion of the sleeve 60.

A wider diameter portion 68 having an external diameter that is larger than an external diameter of other portions of the engagement member 62 is integrally formed at an axial direction upper end portion (left end portion in FIG. 5) of each of the engagement members 62. The wider diameter portions 68 of the engagement members 62 are slidable between the narrow diameter portions 66A, 66B of the sleeves 60.

Moreover, an insertion space 68A is formed at a central portion of an end face of the wider diameter portion 68 at the axial direction upper end portion side of each of the engagement members 62. The insertion space 68A is configured with grooves in a hexagonal shape that enable a tool such as a hex wrench to be inserted therein.

A male threaded portion 64A formed at an axial direction upper end portion (left end portion in FIG. 5) of each of the rods 64 is screwed into a female threaded portion 62A formed at an inner peripheral face of each of the engagement members 62. Note that an abutting portion 70 that abuts to an end face at the axial direction lower end portion side of the wider diameter portion 68 of the engagement member 62 is provided at an end face at the axial direction upper end portion side of each of the rods 64.

The coupling members 58 have lengths that are variable by the engagement members 62 sliding inside the sleeves 60. When the engagement members 62 are sliding, sliding of the engagement members 62 are restricted in both directions along the axial direction of the engagement members 62 by the wider diameter portion 68 of each of the engagement members 62 respectively abutting a lower end portion (right end portion in FIG. 5) of the narrow diameter portions 66A of the sleeves 60, and abutting an upper end portion (left end portion in FIG. 5) of the narrow diameter portion 66B thereof.

Moreover, in order to adjust the position of the rods 64 with respect to the engagement members 62, a hex wrench is inserted into the insertion space 68A of the wider diameter portion 68 of each of the engagement members 62 through the open axial direction upper end portion of the sleeve 60. The engagement members 62 are axially rotated by axially rotating the hex wrench, so as to adjust an amount by which the male threaded portion 64A of each of the rods 64 is screwed into the female threaded portion 62A of each of the engagement members 62.

In the present exemplary embodiment, sliding of the engagement members 62 inside the sleeves 60 are restricted in both directions along the axial direction of the engagement members 62 by the narrow diameter portions 66A, 66B that are formed between the two axial direction end portions at the inner peripheral face of each of the sleeves 60.

This enables the coupling members 58 to be made more compact than configurations in which engagement members such as nuts are provided at an outer side of the sleeves 60, or the engagement members 62 and rods 64 abut at the outer side end portions of the sleeves 60.

Moreover, in the present exemplary embodiment, the axial direction position of the rods 64 can be adjusted with respect to the engagement members 62 by axial rotation of the engagement members 62, while not axially rotating the rods 64. This enables simple adjustment to be made to the length of the coupling members 58 in a state in which the lower eyelet portion 64B of each of the rods 64 is engaged with the flange portion 26 of FIG. 1.

Fifth Exemplary Embodiment

Explanation follows regarding coupling members 78 of a mouthpiece according to a fifth exemplary embodiment of the first aspect, with reference to FIG. 6A to FIG. 7E. Note that explanation will be omitted of configuration similar to that of the coupling members 28, 38, 48, 58 of the first to fourth exemplary embodiments.

As illustrated in FIG. 6A to FIG. 7E, the coupling members 78 each includes a tube shaped sleeve 80 that is open at both axial direction end portions, a tube shaped engagement member 82 provided so as to be slidable inside the sleeve 80, and a rod 84 engaged with the engagement member 82. Note that a sliding member is configured by the engagement member 82 and the rod 84.

Figure 6A:
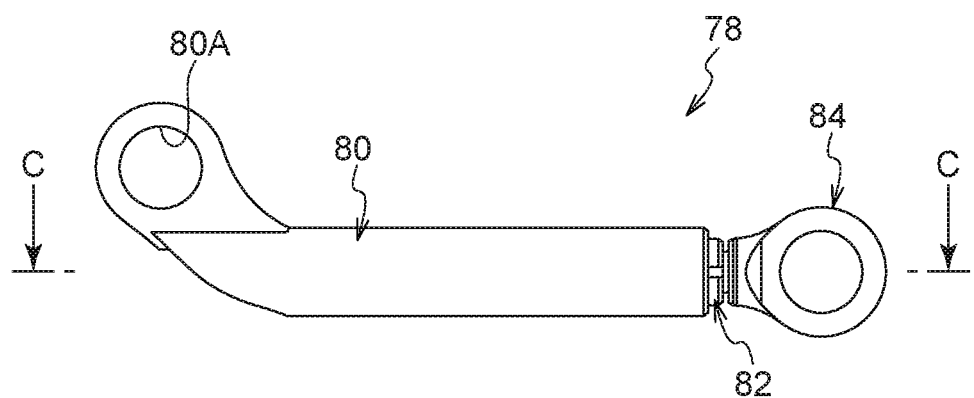
FIG. 6A is a front view illustrating a coupling member of a mouthpiece according to a fifth exemplary embodiment of the first aspect.
Figure 6B:
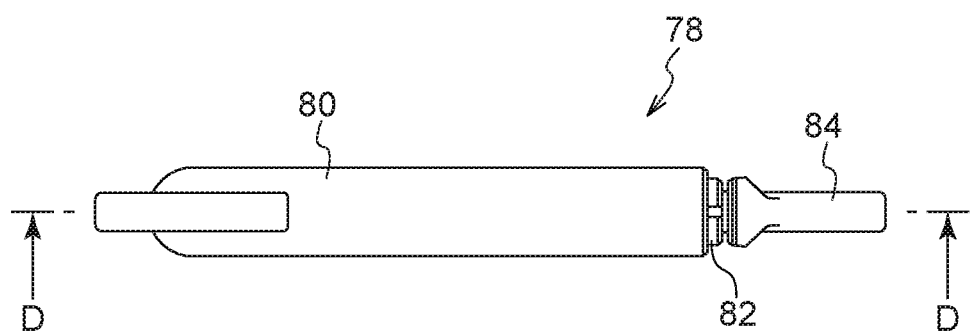
FIG. 6B is a plan view of a coupling member of a mouthpiece according to the fifth exemplary embodiment of the first aspect.
Figure 6C:
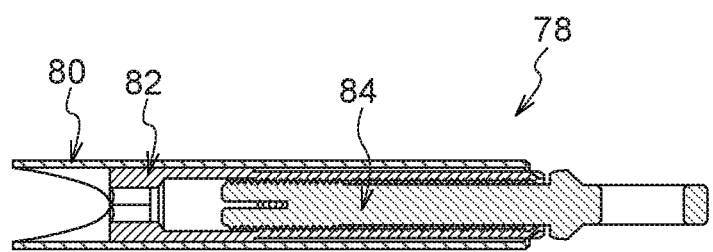
FIG. 6C is cross-section taken on line C-C in FIG. 6A.
Figure 6D:
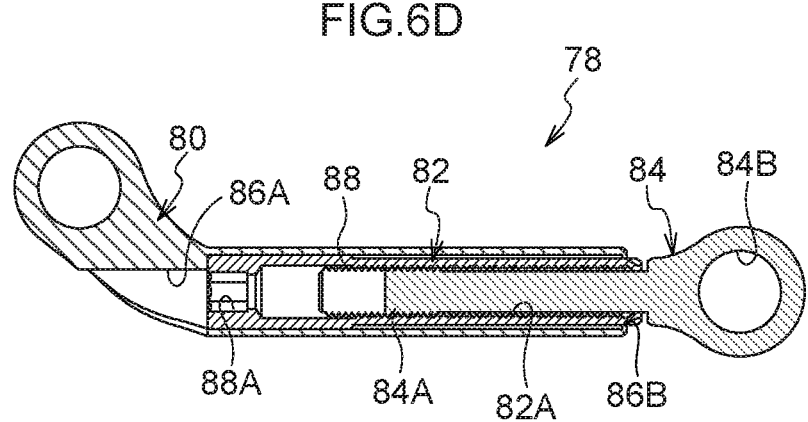
FIG. 6D is a cross-section taken on line D-D in FIG. 6B.
Figure 7D:
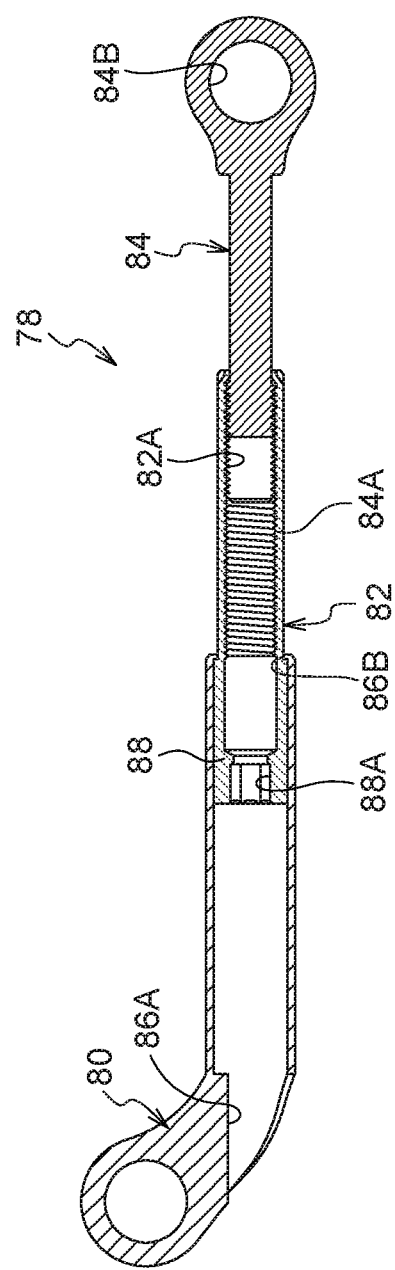
FIG. 7D is a cross-section taken on line F-F of FIG. 7B.

As illustrated in FIG. 6A and FIG. 7A, an upper eyelet portion 80A having a perfect circle shape is formed at a position offset from an axial center of an axial direction upper end portion (lower end portion in FIG. 6A and FIG. 7A) of the sleeve 80. The upper eyelet portion 80A engages with a flange portion at an upper attachment portion of a non-illustrated mouthpiece. As illustrated in FIG. 6D and FIG. 7D, narrow diameter portions 86A, 86B (an example of a restricting section) having internal diameters that are smaller than internal diameters of other portions of the sleeve 80 are formed at an inner peripheral face of each of the sleeves 80 between the two axial direction end portions thereof.

Figure 6E:
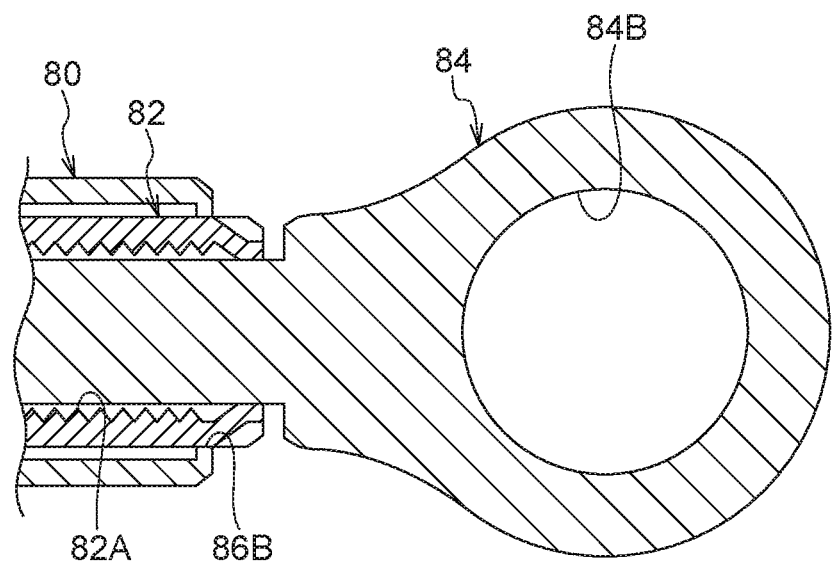
FIG. 6E is an enlarged partial view illustrating an axial direction lower end portion of a sleeve of FIG. 6D.
Figure 6F:
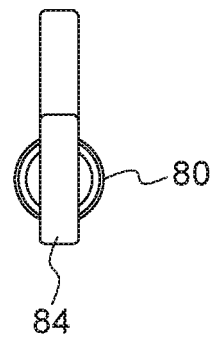
FIG. 6F is a side view illustrating a coupling member of a mouthpiece according to the fifth exemplary embodiment of the first aspect as viewed from the rod side.
Figure 6G:
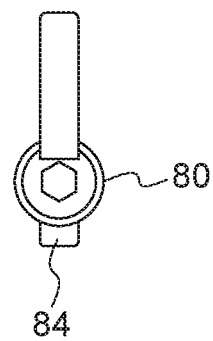
FIG. 6G is a side view illustrating a coupling member of a mouthpiece according to the fifth exemplary embodiment of the first aspect as viewed from the sleeve side.
Figure 6H:
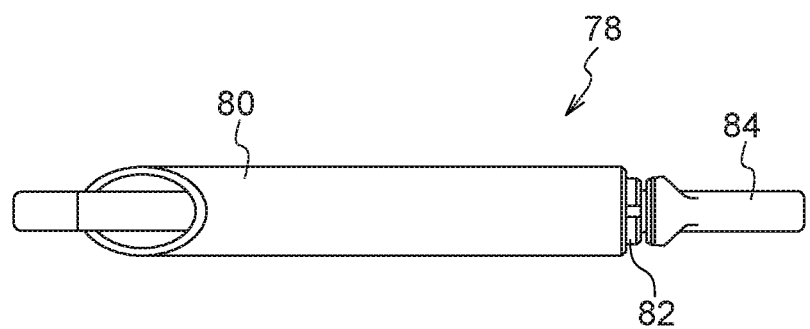
FIG. 6H is a bottom view illustrating a coupling member of a mouthpiece according to the fifth exemplary embodiment of the first aspect.

Note that the narrow diameter portions 86A formed at a lower end side of an axial direction upper end face of each of the sleeves 80 (i.e. at the lower end portion side of the sleeves 80 in FIG. 6D and FIG. 7D) are formed by an increased thickness of wall of the sleeves 80. The narrow diameter portions 86B formed at an upper end side of an axial direction lower end face of each of the sleeves 80 (i.e. at the upper end portion side of the sleeves 80 in FIG. 6D and FIG. 7D) are formed by crimping the axial direction lower end portions of the sleeves 80, as illustrated in FIG. 6E.

As illustrated in FIG. 6D and FIG. 7D, a wider diameter portion 88 having an external diameter that is larger than an external diameter of other portions of the engagement member 82 is integrally formed at an axial direction upper end portion (lower end portion in FIG. 6D and FIG. 7D) of each of the engagement members 82. The wider diameter portions 88 of the engagement members 82 are slidable between the narrow diameter portions 86A, 86B of the sleeves 80.

Moreover, an insertion space 88A is formed at a central portion of an end face of the wider diameter portion 88 at the axial direction upper end portion side of each of the engagement members 82. The insertion space 88A is configured with grooves in a hexagonal shape that enable a tool such as a hex wrench to be inserted therein.

A male threaded portion 84A formed at an axial direction upper end portion (lower end portion in FIG. 6D and FIG. 7D) of each of the rods 84 is screwed into a female threaded portion 82A formed at an inner peripheral face of the engagement members 82. Moreover, a lower eyelet portion 84B having a perfect circle shape is formed at a center axis of the axial direction lower end portion (upper end portion in FIG. 6D and FIG. 7D) of each of the rods 84. The lower eyelet portions 84B each engage with a flange portion at a lower attachment portion of a non-illustrated mouthpiece.

The coupling members 78 have lengths that are variable by the engagement members 82 sliding inside the sleeves 80. When this occurs, sliding of the engagement members 82 are restricted in both directions along the axial direction of the engagement members 82 by the wider diameter portion 88 of each of the engagement members 82 respectively abutting the lower end portion (lower end portion side in FIG. 6D and FIG. 7D) of the narrow diameter portion 86A of the sleeve 80, and abutting the upper end portion (the upper end portion side in FIG. 6D and FIG. 7D) of the narrow diameter portion 86B of the sleeve 80 in each of the engagement members 82.

Moreover, in order to adjust the position of the rods 84 with respect to the engagement members 82, a hex wrench is inserted into the insertion space 88A of the wider diameter portion 88 of each of the engagement members 82 through the open axial direction upper end portion of each of the sleeves 80. The amount that the male threaded portion 84A of each of the rods 84 is screwed into the female threaded portion 82A of each of the engagement members 82 is adjusted by axial rotation of the engagement members 82 by axially rotating the hex wrench.

In the present exemplary embodiment, similarly to in the fourth exemplary embodiment, sliding of the engagement members 82 inside the sleeves 80 can be restricted in both directions along the axial direction of the engagement members 82 by the narrow diameter portions 86A, 86B formed between the two axial direction end portions at the inner peripheral face of each of the sleeves 80.

Moreover, the axial direction position of the rods 84 can be adjusted with respect to the engagement members 82 by axial rotation of the engagement members 82, while not axially rotating the rods 84. This enables simple adjustment to be made to the length of the coupling members 78 in a state in which the lower eyelet portions 84B of the rods 84 are engaged with the flange portions of the non-illustrated mouthpiece.

Other Exemplary Embodiments

Note that the first aspect is not limited to the exemplary embodiments described above, and various other exemplary embodiments are possible within the scope of the present disclosure.

For example, in the first exemplary embodiment, in a non-mounted state of the mouthpiece 10 to the dentition, the upper eyelet portions 30B and the lower eyelet portions 34B are attachable to or detachable from the flange portions 22, 26 of the upper attachment portions 16 and the lower attachment portions 18. However, the upper eyelet portion 30B and the lower eyelet portions 34B may be attached by bonding, screwing, or the like to the flange portions 22, 26 so as to be non-detachable therefrom.

Moreover, in the first exemplary embodiment, the upper attachment portions 16 and the lower attachment portions 18 are formed so as to respectively project out from the outer wall faces 12A, 14A of the maxillary attachment 12 and the mandibular attachment 14. However, the upper attachment portions 16 and the lower attachment portions 18 do not necessarily project from the outer wall faces 12A, 14A of the maxillary attachment 12 and the mandibular attachment 14, and may be provided at inner wall faces of the maxillary attachment 12 and the mandibular attachment 14.

Moreover, in the first exemplary embodiment, the maxillary attachment 12 and the mandibular attachment 14 are respectively mounted to maxillary and mandibular dentition. However, the maxillary attachment 12 and the mandibular attachment 14 may be mounted to maxillary and mandibular gums instead of the maxillary and mandibular dentition, or may be mounted to a separate member such as a dental brace that has been mounted to the dentition.

Moreover, although the upper eyelet portions 30B are each formed at a position offset from the axial center of the respective sleeve 30, the upper eyelet portion 30B may be formed at the central axis of the sleeve 30. Similarly, although the lower eyelet portions 34B are each formed on the center axis of the respective rods 34, the lower eyelet portion 34B may be formed at a position offset from the axial center of the rod 34. Furthermore, a configuration may be adopted in which the amount by which the male threaded portion 34A is screwed in is confirmed by looking at the position of the upper end of the male threaded portion 34A through the opening 32C of the engagement member 32, without forming the scale 36A on each of the rods 34.

Moreover, although in the first to the fourth exemplary embodiments the upper eyelet portions 30B, 40B, 50A and the lower eyelet portions 34B, 44B, 54B, 64B are respectively configured with ellipsoidal shapes, they may be configured with perfect circle shapes similarly to the upper eyelet portion 80A and the lower eyelet portion 84B of the fifth exemplary embodiment.

Similarly, although in the first exemplary embodiment the flange portions 22, 26 of the upper attachment portions 16 and the lower attachment portions 18 are configured with ellipsoidal shapes, they may be configured with perfect circle shapes. Moreover, the upper attachment portions 16 and the lower attachment portions 18 may be respectively attachable to or detachable from the maxillary attachment 12 and the mandibular attachment 14.

Specifically, for example, part of nuts that include female threaded portions may be embedded in outer wall faces 12A, 14A of the maxillary attachment 12 and the mandibular attachment 14. An upper attachment portion and a lower attachment portion are then configured by bolts that include a shaft portion formed with a male threaded portion and a head portion (namely, flange portion) that has a perfect circle shape and is provided at the leading end of the shaft portion. This enables the upper attachment portion and the lower attachment portion to be attached to the maxillary attachment 12 and the mandibular attachment 14 by screwing the male threaded portions of these bolts into the female threaded portions of the nuts.

Moreover, in the fourth exemplary embodiment, the narrow diameter portions 66A are formed by increasing the thickness of the wall of the sleeves 60, and the narrow diameter portions 66B are formed by crimping the lower end portions of the sleeves 60. However, the methods of forming the narrow diameter portions 66A, 66B are not limited to the methods of the exemplary embodiments described above, and the narrow diameter portions 66A, 66B may be formed by the same method as each other. Moreover, although the wider diameter portions 68 are integrally formed at the engagement members 62, a configuration may be adopted in which wider diameter portions 68 that are separate members are joined to axial direction upper end portions of the engagement members 62.

Moreover, in the exemplary embodiments described above, the restricting section is configured by the slits 30A, 40A, the stoppers 56A, 56B, or the narrow diameter portions 66A, 66B, 86A, 86B. However, the restricting section may be formed in any shape as long as the restricting section is formed between the two axial direction end portions of the sleeves 30, 40, 50, 60, 80, namely between one axial direction end face and another axial direction end face thereof, and the restricting section has a configuration in which sliding of the engagement member (sliding member) can be restricted in both directions along the axial direction of the engagement member.

Moreover, in the first to the fifth exemplary embodiments, the male threaded portions 34A, 44A, 54A, 64A, 84A are formed at the rods 34, 44, 54, 64, 84, and the female threaded portions 32B, 42A, 52A, 62A, 82A are formed at the engagement members 32, 42, 52, 62, 82. However, female threaded portions may be formed at the rods 34, 44, 54, 64, 84 and male threaded portions may be formed at the engagement members 32, 42, 52, 62, 82.

Moreover, in the first to the fifth exemplar) embodiments, the sliding members are configured by separate members of the engagement members 32, 42, 52, 62, 82 and the rods 34, 44, 54, 64, 84 that screw together, such that the length of the sliding members is adjustable by adjusting the amount screwed in. However, the sliding members may be configured by a single member that is not adjustable in length.

Moreover, the materials for configuring the maxillary attachment 12 and the mandibular attachment 14, the upper attachment portions 16, the lower attachment portions 18, and the coupling members 28 are not limited to the examples of materials given in the exemplary embodiments described above. For example, although the upper attachment portions 16, the lower attachment portions 18, and the coupling members 28 are made of metal, they may be configured from a plastic from the perspectives of enabling application to patients with metal allergies, achieving a saving in weight while also retaining the strength of members, or reducing any feeling of discomfort inside the oral cavity.

Second Aspect

A mouthpiece according to a second aspect of the present disclosure includes a maxillary attachment that mounts to a maxilla, a mandibular attachment that mounts to a mandible, an upper attachment portion provided at the maxillary attachment, a lower attachment portion provided at the mandibular attachment, and a coupling member that is attached to the upper attachment portion and the lower attachment portion. In the second aspect, at an attachment angle of the coupling member in a mounted state of the maxillary attachment and the mandibular attachment to the maxilla and the mandible, the coupling member is suppressed from attaching to or detaching from the upper attachment portion and the lower attachment portion. Further, is disposed at an attachment angle of the coupling member in a non-mounted state of the maxillary attachment and the mandibular attachment to the maxilla and the mandible, the coupling member is attachable to or detachable from at least one of the upper attachment portion or the lower attachment portion.

The second aspect enables the maxillary attachment and the mandibular attachment to be easily separated from each other due to the coupling member being attachable to or detachable from at least one of the upper attachment portion or the lower attachment portion at the attachment angle in the non-mounted state of the maxillary attachment and the mandibular attachment to the maxilla and the mandible.

The mouthpiece according to an exemplary embodiment of the second aspect is configured similarly to the mouthpiece 10 of the first exemplary embodiment of the first aspect as illustrated in FIG. 1 to FIG. 3C, and so explanation will be omitted thereof.

Note that the second aspect is not limited to the exemplary embodiments described above, and various other exemplary embodiments may be implemented within the scope of the present disclosure.

For example, in the exemplary embodiments described above, as illustrated in FIG. 1 to FIG. 3C, the flange portions 22, 26, the upper eyelet portions 30B, and the lower eyelet portions 34B are formed in similar ellipsoidal shapes to each other. However, the flange portions 22, 26, the upper eyelet portions 30B, and the lower eyelet portions 34B may be formed in any shape that suppress attaching or detaching of the coupling members 28 when the mouthpiece 10 is in a mounted state to the dentition, and that enables the coupling members 28 to be easily attachable or detachable in the non-mounted state of the mouthpiece 10.

Moreover, both the upper eyelet portions 30B and the lower eyelet portions 34B are attachable to or detachable from the flange portions 22, 26 when the mouthpiece 10 is in the non-mounted state to the dentition. However, only one of the upper eyelet portions 30B and the lower eyelet portions 34B needs to be attachable and detachable, and the other may be attached by bonding, screwing, or the like to the upper attachment portions 16 or the lower attachment portions 18 so as to be substantially non-detachable therefrom.

Moreover, in the above exemplary embodiments the upper attachment portions 16 and the lower attachment portions 18 are formed so as to project out from the outer wall faces 12A, 14A of the maxillary attachment 12 and the mandibular attachment 14. However, the upper attachment portions 16 and the lower attachment portions 18 do not necessary project out from the outer wall faces 12A, 14A of the maxillary attachment 12 and the mandibular attachment 14, and may be provided at the inner wall faces of the maxillary attachment 12 and the mandibular attachment 14.

Moreover, although the upper eyelet portions 30B are formed at positions offset from the axial center of the sleeves 30, the upper eyelet portions 30B may each be formed at the center axis of the respective sleeve 30. Furthermore, although the directions of the major diameter of in the upper eyelet portions 30B and the lower eyelet portions 34B are oriented in the same direction as the length directions of the coupling members 28, a configuration may be adopted in which the major diameter directions are directions orthogonal to the length directions of the coupling members 28, or the like.

Moreover, the method of adjusting the length of the coupling members 28 is not limited to that of the exemplary embodiments described above. Furthermore, a configuration may be adopted in which the amount by which the male threaded portion 34A is screwed in is confirmed by looking at the position of the upper end of the male threaded portion 34A through the opening 32C of the engagement member 32, without forming the scale 36A on each of the rods 34.

The entire disclosures of Japanese Patent Application Nos. 2016-141424 and 2016-141425 filed Jul. 19, 2016 are incorporated by reference in this specification.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. A coupling member comprising:
a sliding member having a first axial direction end portion that is configured to be coupled to a first attachment portion provided at a first attachment that is adapted to be mounted to one of a maxilla or a mandible; and
a sleeve having a first axial direction end portion that is configured to be coupled to a second attachment portion provided at a second attachment that is adapted to be mounted to the other of the maxilla or the mandible, the sliding member being inserted into the sleeve so as to be slidable, and a restricting section being formed at the sleeve between two axial direction end portions of the sleeve so as to restrict sliding of the sliding member in both directions along an axial direction of the sliding member,
wherein the sliding member is configured by a rod and a tube shaped engagement member, the rod having the first axial direction end portion coupled to the first attachment portion and being formed with a screw portion at a second axial direction end portion, and the tube shaped engagement member having a screw receiving portion, formed at an inner peripheral face at a first axial direction end portion of the tube shaped engagement member, into which the screw portion of the rod is screwed,
wherein the first axial direction end portion of the sleeve is open, and an insertion space is formed at a second axial direction end portion of the tube shaped engagement member for a tool that is configured to be inserted into the insertion space,
wherein the insertion space is open at an end face at the second axial direction end portion of the tube shaped engagement member,
wherein the tube shaped engagement member is configured to be rotated with respect to the rod, by the tool that is inserted from the end face at the second axial direction end portion of the tube shaped engagement member into the insertion space, such that a length of the sliding member is adjustable, and
wherein the restricting section is configured by narrow diameter portions that have smaller internal diameters than internal diameters of other portions of the sleeve are formed at two locations at an inner peripheral face of the sleeve between the first and second end portions in the axial direction thereof, and a wider diameter portion having an external diameter that is larger than an external diameter of other portions of the engagement member is integrally formed at the second axial direction end portion of the engagement member such that the wider diameter portion is configured to abut the narrow diameter portions of the sleeve, and that the wider diameter portion is configured to be slid on the inner peripheral face of the sleeve between the narrow diameter portions; wherein the wider diameter portion is configured to receive the tool in the axial direction.

2. The coupling member of claim 1, wherein:
the first attachment portion is formed projecting out from an outer wall face of the first attachment;
the second attachment portion is formed projecting out from an outer wall face of the second attachment.

3. The coupling member of claim 1, wherein the tube shaped engagement member is rotatable about an axis, and an amount that the screw portion of the rod is screwed into the screw receiving portion of the tube shaped engagement member is adjustable by rotation about the axis of the tube shaped engagement member.

4. The coupling member of claim 1, wherein:
the screw portion of the rod is a male threaded portion having a scale formed thereon;
the screw receiving portion of the tube shaped engagement member is a female threaded portion; and
an opening is formed at an outer peripheral face of the tube shaped engagement member at the first axial direction end portion of the tube shaped engagement member.

5. A mouthpiece comprising:
the coupling member of claim 1;
a mandibular attachment serving as the first attachment;
a maxillary attachment serving as the second attachment;
the first attachment portion projecting from an outer wall face of the mandibular attachment; and
the second attachment portion projecting from an outer wall face of the maxillary attachment.

6. A mouthpiece comprising:
a maxillary attachment adapted to be mounted to a maxilla;
a mandibular attachment adapted to be mounted to a mandible;
an upper attachment portion provided at the maxillary attachment;
a lower attachment portion provided at the mandibular attachment; and
the coupling member of claim 1, wherein:
the coupling member is attached to the upper attachment portion and the lower attachment portion,
at an attachment angle of the coupling member in a mounted state of the maxillary attachment and the mandibular attachment to the maxilla and the mandible, the coupling member is suppressed from attaching to or detaching from the upper attachment portion and the lower attachment portion, and
at an attachment angle of the coupling member in a non-mounted state of the maxillary attachment and the mandibular attachment to the maxilla and the mandible, the coupling member is attachable to or detachable from at least one of the upper attachment portion or the lower attachment portion.

7. The mouthpiece of claim 6, wherein the upper attachment portion is formed projecting out from an outer wall face of the maxillary attachment, and the lower attachment portion is formed projecting out from an outer wall face of the mandibular attachment.

8. The mouthpiece of claim 6, wherein:
at least one of the upper attachment portion or the lower attachment portion includes a shaft portion provided with a flange portion having a long axis and a short axis and provided in a vicinity of a leading end of the shaft portion; and
the coupling member includes an eyelet portion that is engaged with the flange portion, the eyelet portion having a major diameter that is longer than a length of the long axis of the flange portion and having a minor diameter that is longer than a length of the short axis of the flange portion and that is shorter than the length of the long axis of the flange portion.

9. The mouthpiece of claim 8, wherein the flange portion is able to pass through the eyelet portion when a long axis direction of the flange portion is aligned with a major diameter direction of the eyelet portion.

10. The mouthpiece of claim 8, wherein the flange portion is formed in a similar shape to a shape of the eyelet portion.

11. The mouthpiece of claim 10, wherein the flange portion and the eyelet portion are formed with ellipsoidal shapes.

12. The mouthpiece of claim 8, wherein:
a major diameter direction of the eyelet portion is configured along a length direction of the coupling member; and
the flange portion is configured such that an angle of the long axis of the flange portion with respect to an opposing face of the maxillary attachment, opposing the mandibular attachment, or with respect to an opposing face of the mandibular attachment, opposing the maxillary attachment, is outside of a range of from 10 degrees to 60 degrees.

* * * * *